US012697453B2

(12) United States Patent　　　(10) Patent No.: US 12,697,453 B2
　　Kwok et al.　　　(45) Date of Patent: Aug. 4, 2026

(54) OXYGEN MASK HAVING BITE BLOCK AND MONITORING

(71) Applicant: TELEFLEX LIFE SCIENCES LLC, Wilmington, DE (US)

(72) Inventors: Kien Chung Kwok, Singapore (SG); Aviram Elbaz, Apex, NC (US)

(73) Assignee: TELEFLEX LIFE SCIENCES LLC, Wilmington, DE (US)

( * ) Notice: Subject to any disclaimer, the term of this patent is extended or adjusted under 35 U.S.C. 154(b) by 896 days.

(21) Appl. No.: 17/747,553

(22) Filed: May 18, 2022

(65) Prior Publication Data

US 2022/0370746 A1　　Nov. 24, 2022

Related U.S. Application Data

(60) Provisional application No. 63/189,763, filed on May 18, 2021.

(51) Int. Cl.
　　*A61M 16/06*　　(2006.01)
　　*A61M 16/04*　　(2006.01)
　　*A61M 16/08*　　(2006.01)
(52) U.S. Cl.
　　CPC ........ *A61M 16/06* (2013.01); *A61M 16/0493* (2014.02); *A61M 16/0841* (2014.02)
(58) Field of Classification Search
　　CPC ...................... A61M 16/0493; A61M 16/0495
　　See application file for complete search history.

(56) References Cited

U.S. PATENT DOCUMENTS

| | | | | | |
|---|---|---|---|---|---|
| 4,062,357 | A | * | 12/1977 | Laerdal | A61M 16/0683 |
| | | | | | 128/206.26 |
| 4,895,565 | A | * | 1/1990 | Hillstead | A61M 39/0606 |
| | | | | | 604/167.04 |
| 5,121,745 | A | * | 6/1992 | Israel | A61M 16/06 |
| | | | | | 128/202.28 |
| 5,431,158 | A | * | 7/1995 | Tirotta | A61M 16/0488 |
| | | | | | 128/207.14 |
| 6,039,044 | A | * | 3/2000 | Sullivan | A61M 16/06 |
| | | | | | 128/205.25 |
| 6,517,549 | B1 | * | 2/2003 | Dennis | A61M 16/0493 |
| | | | | | 128/200.26 |
| 6,758,212 | B2 | | 7/2004 | Swann | |

(Continued)

FOREIGN PATENT DOCUMENTS

| | | | | |
|---|---|---|---|---|
| CN | 206239854 U | | 6/2017 | |
| KR | 20190030427 A | * | 3/2019 | A62B 23/02 |
| WO | 2020/162942 A1 | | 8/2020 | |

*Primary Examiner* — Bradley H Philips
(74) *Attorney, Agent, or Firm* — BakerHostetler

(57) ABSTRACT

An oxygen mask may include a convex shell having an upper portion and a lower portion and defining a chamber, a rim at least partially around the chamber, a nasal access port in the upper portion, and an oral access port in the lower portion. The nasal access port that is penetratable and/or puncturable to provide access to the chamber, and the oral access port may include a bite block defining a lumen and a valve in the lumen. The oxygen mask may include an inlet into the chamber, an outlet from the chamber, and a sampling port in communication with the chamber. The oxygen mask may include at least one fold or crease configured to allow the bite block to tilt relative to the horizontal axis and/or to translate along the vertical axis.

23 Claims, 7 Drawing Sheets

(56) References Cited

U.S. PATENT DOCUMENTS

| 8,950,403 | B2 * | 2/2015 | Howard ................ A61M 16/06 |
| | | | 128/206.24 |
| 2002/0162556 | A1 | 11/2002 | Smith et al. |
| 2002/0170557 | A1 * | 11/2002 | Schmidt ............ A61M 15/0018 |
| | | | 128/200.23 |
| 2005/0217678 | A1 * | 10/2005 | McCormick ...... A61M 16/0841 |
| | | | 128/206.29 |
| 2006/0054168 | A1 * | 3/2006 | Yu ......................... A61M 16/06 |
| | | | 128/206.28 |
| 2008/0108939 | A1 * | 5/2008 | Moulton ............. A61M 39/045 |
| | | | 604/43 |
| 2012/0060843 | A1 | 3/2012 | Magidson et al. |
| 2012/0330111 | A1 * | 12/2012 | Borody ............. A61M 16/0488 |
| | | | 600/300 |
| 2013/0172768 | A1 * | 7/2013 | Lehman ................ A61M 16/06 |
| | | | 128/205.25 |
| 2014/0196726 | A1 * | 7/2014 | Mallek .................. A61M 16/06 |
| | | | 29/428 |
| 2017/0007795 | A1 | 1/2017 | Pedro et al. |
| 2017/0197052 | A1 * | 7/2017 | Tylka ................. A61M 16/0497 |
| 2018/0021606 | A1 * | 1/2018 | Eisenkraft ............ A62B 18/025 |
| | | | 128/206.28 |
| 2018/0333553 | A1 * | 11/2018 | Brown ............... A61B 1/00165 |
| 2020/0261678 | A1 * | 8/2020 | Chang .................. A61M 16/06 |
| 2021/0023319 | A1 * | 1/2021 | Brar ...................... A61M 16/06 |

* cited by examiner

OXYGEN MASK HAVING BITE BLOCK AND MONITORING

PRIORITY

The present disclosure claims priority to U.S. Provisional Patent Application No. 63/189,763, filed on May 18, 2021, the entire disclosure of which is expressly incorporated herein by reference.

TECHNICAL FIELD

The present disclosure relates generally to face masks, and more particularly to oxygen face masks having an integrated bite block and/or monitoring.

BACKGROUND

Procedures often require delivery of oxygen to a patient to prevent hypoxia (low oxygen tension in the blood and tissue). Hypoxia can be of critical importance if the patient does not breathe adequately to maintain oxygen tension, as prolonged low oxygen tension can lead to an abnormal heart rhythm, cardiac arrest and/or respiratory arrest. Endoscopic procedures may additionally require access to the mouth or nose of the patient for insertion of instruments.

Overview

The present inventors recognize that there is a need for improvements to address inefficiencies of current face masks that provide oxygen delivery or access to the mouth or nose. The present inventors also recognize a need for an improved fit to ensure access to the mouth and/or nose given the variability in facial structures and shapes. Additional improvements of the present invention over the state-of-art can be readily recognized in the disclosure provided herein.

Thus, a first aspect of the present invention is directed to a mask that may include a convex shell having an upper portion and a lower portion and defining a chamber, a rim at least partially around the chamber, a nasal access port in the upper portion, and an oral access port in the lower portion. The nasal access port may be penetratable and/or puncturable to provide access to the chamber, and the oral access port may include a bite block defining a lumen and a valve in the lumen.

A second aspect of the present invention is directed to a mask that may include a convex shell having upper portion and a lower portion and defining a chamber, a rim at least partially around the chamber, an inlet into the chamber, an outlet from the chamber, a sampling port in communication with the chamber, a nasal access port in the upper portion, and an oral access port in the lower portion. The nasal access port may be penetratable and/or puncturable to provide access to the chamber, and the oral access port may include a bite block defining a lumen and a duckbill valve in the lumen.

A third aspect of the present invention is directed to a mask that may include a convex shell having an upper portion and a lower portion and defining a chamber, a rim at least partially around the chamber, an oral access port in the lower portion, and at least one fold or crease. The oral access port may include a bite block defining a lumen and a valve in the lumen, and the at least one fold or crease may be configured to allow the bite block to tilt relative to a horizontal axis and/or to translate along a vertical axis.

Some embodiments of the masks include an inlet into the chamber; and an outlet from the chamber. In some embodiments, the outlet includes a plurality of holes disposed around a post. In some embodiments, the mask includes a sampling port in communication with the chamber. In some embodiments, the mask includes at least one post on the upper portion configured to secure a nose clip. In some embodiments, the nasal access port includes one or more flaps having edges that form a plurality of lines. In some embodiments, the plurality of lines includes a first line and a second line that are connected at a first node and a third line and a fourth line that are connected at a second node. In some embodiments, the plurality of lines includes at least two lines that are connected at an angle in a non-perpendicular orientation. In some embodiments, the plurality of lines includes a first line and a second line that are connected to form a first "V" shape. In some embodiments, the plurality of lines includes a third line and a fourth line that are connected to form a second "V" shape. In some embodiments, the second line and the third line are connected to form a "W" shape. In some embodiments, the one or more flaps are connected by one or more frangible portions along at least a portion of the edges. In some embodiments, the valve is a duckbill valve. In some embodiments, the bite block extends at an acute angle relative to a horizontal axis of the mask. In some embodiments, the mask includes at least one fold or crease configured to allow the bite block to tilt relative to the horizontal axis and/or to translate along the vertical axis. In some embodiments, the at least one fold or crease is configured to allow the bite block to tilt relative to the horizontal axis and to translate along the vertical axis. In some embodiments, the at least one fold or crease extends above and/or below the oral access port. In some embodiments, the at least one fold or crease laterally overlaps the bite block. In some embodiments, the at least one fold or crease extends circumferentially around the bite block. In some embodiments, the mask further includes a membrane forming the at least one fold or crease. In some embodiments, the at least one fold or crease includes a plurality of folds or creases. In some embodiments, the plurality of folds or creases extend laterally between a first side portion and a second side portion.

BRIEF DESCRIPTION OF THE DRAWINGS

In order that the invention may be readily understood, aspects of this invention are illustrated by way of examples in the accompanying drawings.

DETAILED DESCRIPTION

Figures 1, 2:
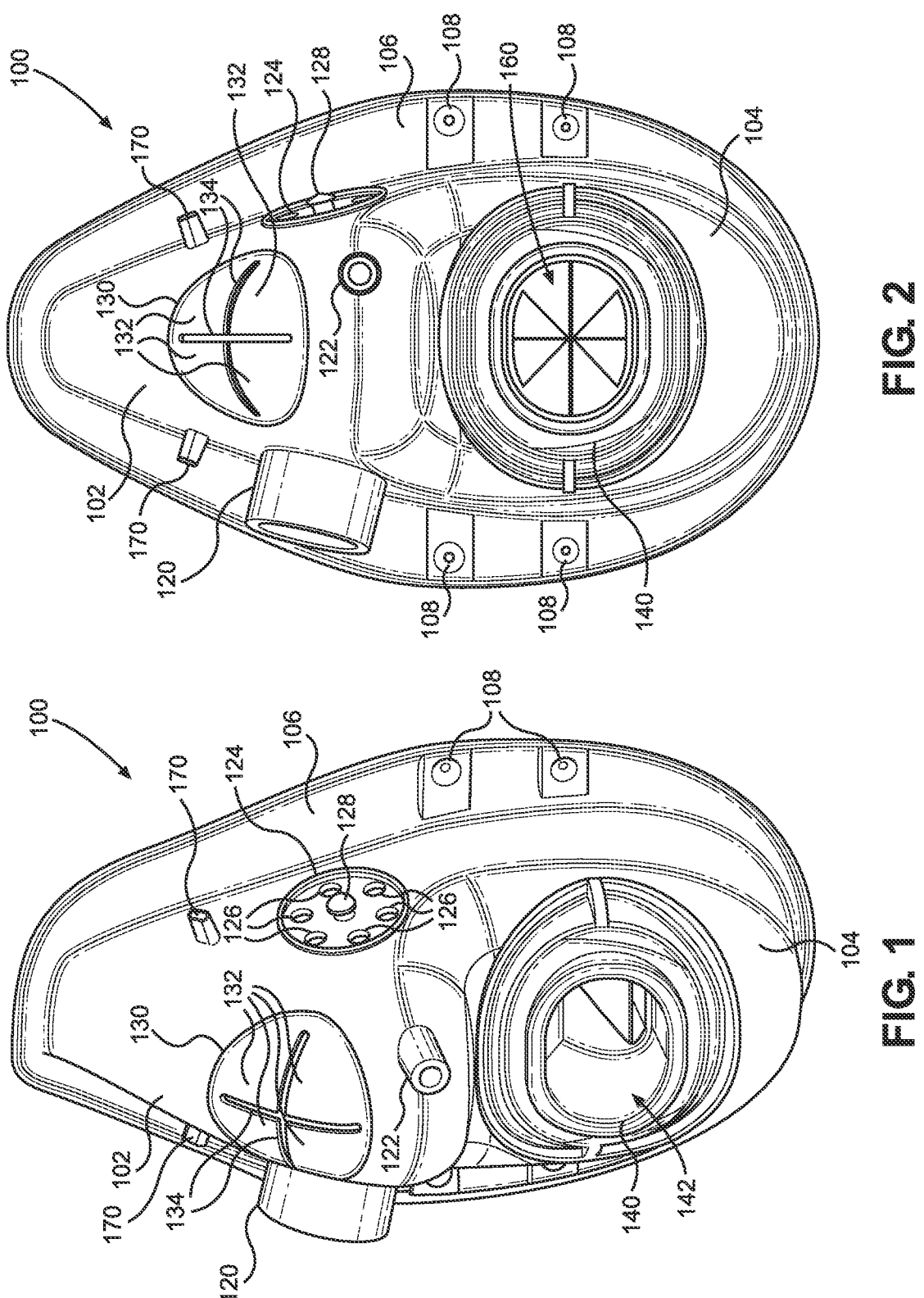
FIG. 1 illustrates an exemplary frontal isometric view of a first embodiment of an oxygen mask according to the present invention.
FIG. 2 illustrates a frontal view of the oxygen mask of FIG. 1.

The present invention is directed to a multi-access port oxygen mask having an integrated oral bite block that may be used as a non-rebreather mask. The oxygen mask may be worn as a standard oxygen mask during traditional oxygen therapy, yet quickly converted into an intubation mask. Thus, the oxygen mask may selectively allow access to a mouth and/or nose of a patient for insertion of an instrument (e.g., catheters, endoscopes, and/or probes) during oxygen delivery. A duckbill valve may be configured in-line and integrated into the bite block to prevent outflow of gases through the oral access port. When the instrument is inserted through the oral access port, the duckbill valve may flex open under pressure from the instrument and be biased into a closed configuration when the instrument is removed. When oxygen supply to the patient is insufficient or disrupted, the duckbill valve may further serve as a safety valve which opens under negative pressure within the face mask to allow ambient room air to enter the face mask during the inspiratory cycle. The nasal access may include one or more flaps having edges that form a plurality of nodes that are penetrated and/or punctured. The nodes may be in-line with the nasal cavities to provided selective access to each nasal cavity. The clinician may manually penetrate and/or puncture the nasal diaphragm and/or use the integral bite block as points of entry for a variety of procedures involving nasally or orally introduced instruments, without disturbing the ongoing benefits of increased oxygen saturation and/or continuous monitoring of expired gases. In some embodiments, the bite block is configured to tilt (or pivot) and/or translate to adjust to the relative position of the mouth of the patient by being attached to at least one fold or crease and/or a flexible membrane. In some embodiments, the bite block is configured to vertically tilt at least up to about 5-8 degrees relative to a horizontal axis of the mask. In some embodiments, the bite block is configured to vertically tilt at least up to about 11-15 degrees relative to the horizontal axis of the mask. In some embodiments, the bite block is configured to vertically tilt at least up to about 25 degrees relative to the horizontal axis of the mask. In some embodiments, the mask is configured to maintain the adjustment (pivot angle and/or translation distance) without immediately reverting back to the original configuration, so the bite block may be adjusted prior to being placed on the patient. The oxygen mask may further include a multiple-inlet port having an oxygen tube connector attachable to a reservoir bag, a carbon dioxide sampling port, an exhaust port, and/or a nose clip.

Terms "upper" or "above" as used herein describe a portion of the mask or its components that is closer relative to the top of the head of the patient when used as intended.

Terms "lower" or "below" as used herein describes a portion of the mask or its components that is closer to the chin of the patient when used as intended. The term "vertical" as used herein describes the axis of direction extending along or parallel to a medial or sagittal plane of the patient extending in a direction extending between the chin and the head when used as intended. The term "lateral" or "horizontal" describes a relative portion of the mask or its components extending along or parallel to a horizontal or transverse plane of the patient when used as intended.

Figures 5, 6:
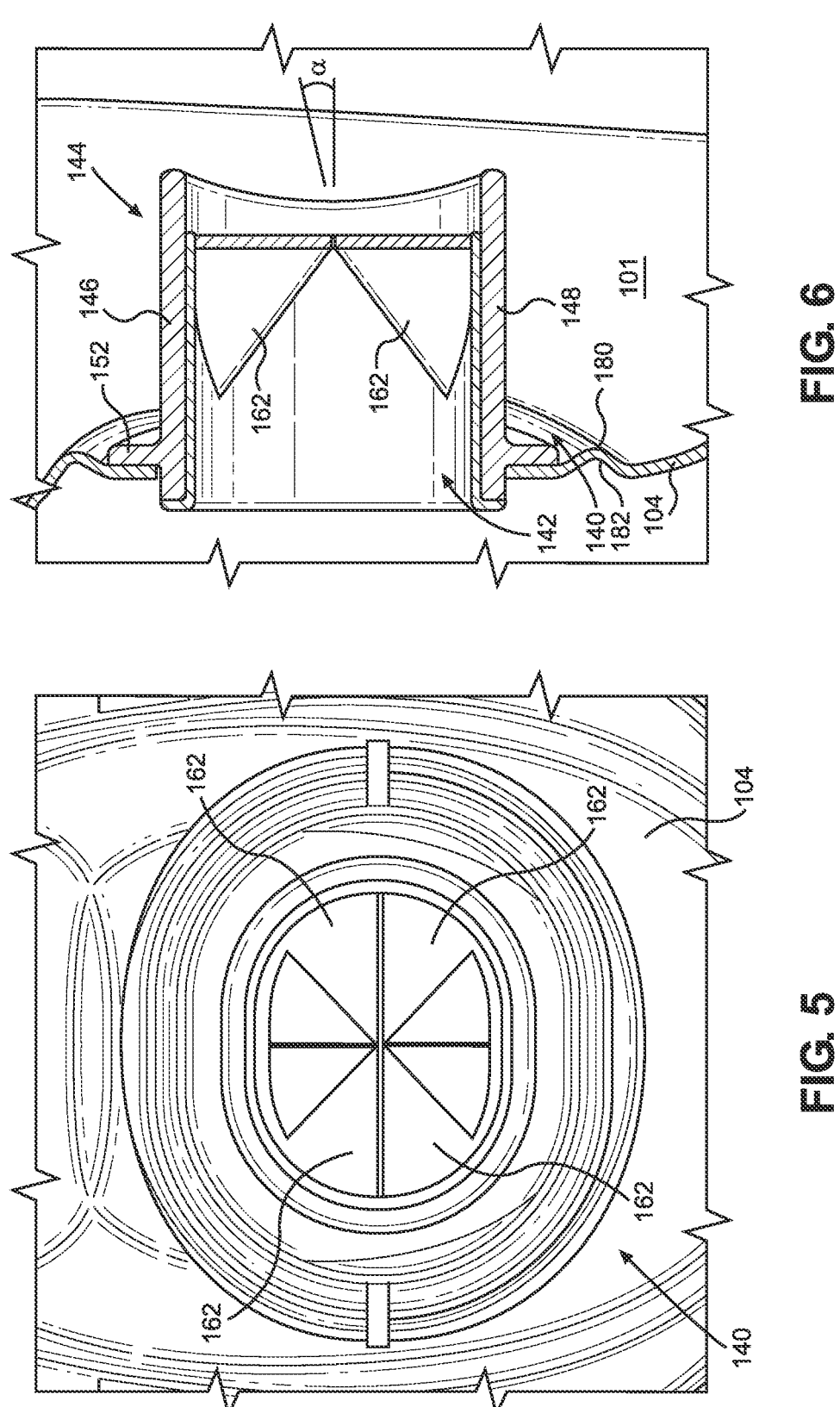
FIG. 5 illustrates an exemplary frontal partial view of the oxygen mask of FIGS. 1-4.
FIG. 6 illustrates an exemplary side cross-sectional partial view of the oxygen mask of FIGS. 1-5.
Figures 7, 8:
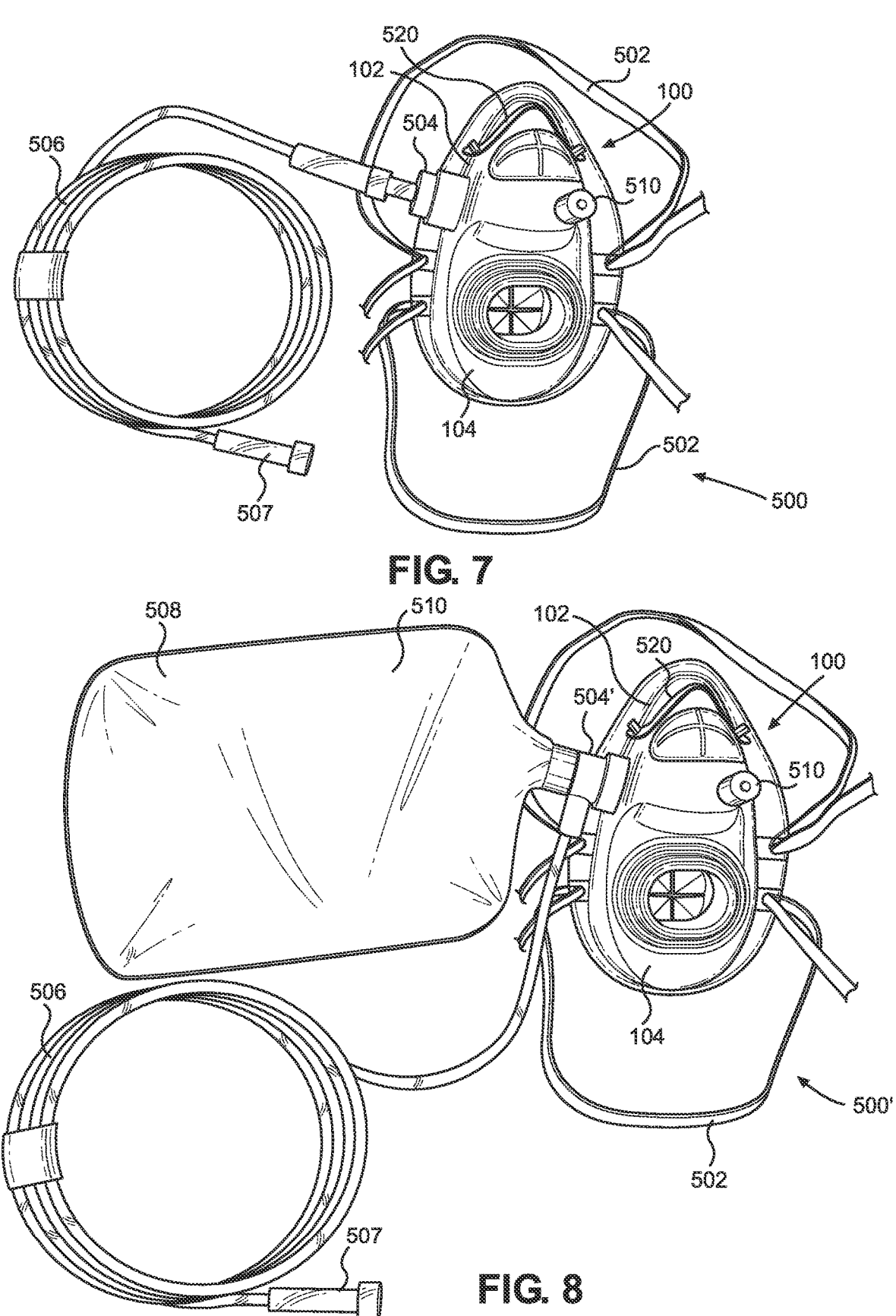
FIG. 7 illustrates a first exemplary assembly including the oxygen mask of FIGS. 1-6.
FIG. 8 illustrates a second exemplary assembly including the oxygen mask of FIGS. 1-6.

FIGS. 1-6 illustrate an oxygen face mask 100 according to a first exemplary embodiment of the present invention. FIG. 7 illustrates a first oxygen system 500 including the oxygen mask 100, and FIG. 8 illustrates a second oxygen system 500' including the oxygen mask 100. The oxygen mask 100 may include a convex shell having an upper portion 102 and a lower portion 104 and defining a chamber 101 that fits over the face of a patient. The upper portion 102 may have a convexity to fit over a nose of the patient with sufficient space for comfort. The lower portion 104 may be configured to fit over a mouth of the patient. A rim 106 may extend at least partially (e.g. fully) around the upper portion 102 and the lower portion 104. In use, the rim 106 may engage the face of the patient to create an air-tight seal when the oxygen mask 100 generally envelops the nose and mouth of the patient in the chamber 101. The oxygen mask 100 may have one or more inlets and/or outlets in communication with the chamber 101 to deliver oxygen-rich air to the patient. For example, the oxygen mask 100 may include an oxygen supply port 120 providing an inlet to the chamber 101, a sampling port 122 providing an outlet of the chamber 101, and an exhalation port 124 providing an outlet of the chamber 101, as further discussed below with reference to FIGS. 7 and 8.

The oxygen mask 100 may include a nasal access port 130 in the upper portion 102. The nasal access port 130 may be penetratable and/or puncturable. For example, as illustrated, the nasal access port 130 may include one or more flaps 132 connected by one or more frangible portions 134 along at least a portion of the edges of the one or more flaps 132. The one or more frangible portions 134 may be normally intact to ensure the one or more flaps 132 are held together and seal the nasal access port 130, preventing the release of gas therethrough. The one or more frangible portions 134 may be made of a different material (e.g., a softer or weaker material) and/or have reduced material strength provided by a reduced thickness, compared to the one or more flaps 132 and/or the shell of the oxygen mask 100. In some embodiments, the one or more frangible portions 134 may be an adhesive or weld connecting the one or more flaps 132. The one or more frangible portions 134 may be selectively torn or broken to separate the one or more flaps 132 to provide one or more access openings to the nasal passage(s) for insertion of an instrument (e.g., a catheter, an endoscope, and/or a probe). The one or more flaps 132 may be biased in the naturally closed configuration. Thus, the one or more flaps 132 may be sufficiently flexible to conform around the inserted instrument to ensure that the chamber 101 is sealed and revert back into the closed configuration after the instrument is removed. As further illustrated, the one or more frangible portions 134 and/or edges of the one or more flaps 132 may form first and second lines extending perpendicular to each other and crossing at a single node to form a "+" or "X" shape. A portion of each of the lines may be separately penetrated and/or punctured while another portion of the same line remains intact or approximated reducing the escape of oxygen.

In some embodiments with the one or more frangible portions 134, the nasal access port 130 may have a continuous, flexible, modifiable membrane formed by the one or more flaps 132 when the one or more frangible portions 134 are intact, from which one or more customized instrument-access openings may be manually constructed when and if needed, by puncturing one or more lengths of the one or more frangible portions 134 to access either or both of the left and right nasal cavities of the patient. In some embodiments, the one or more flaps 132 and/or the one or more frangible portions 134 may be made of the same material as the shell of the oxygen mask 100 and integrally formed, for example, through injection molding of the oxygen mask 100.

In some embodiments, the one or more frangible portions 134 may be omitted, such that the edges of the one or more flaps 132 may be approximated to produce small gaps providing a sufficient seal to reduce gas leakage. The small gaps formed between the one or more flaps 132 and the inserted instrument resulting with a minor amount of gas leakage in and out of the oxygen mask 100; however, the gas leakage through the small gaps would be negligible compared to the oxygen made available to the patient through the oxygen supply port 120. The small gaps between the one or more flaps 132 may form lines having the same orientation as the one or more frangible portions 134. Alternatively, the frangible portions 134 may be formed just at the node to connect the one or more flaps 132 and retain the shape of the nasal access port 130 during shipping and storage.

In some embodiments, the one or more flaps 132 may be omitted, and the membrane covering the nasal access port 130 may be a single, continuous frangible portion 134 (not illustrated) allowing for completely customizable access openings of any size and shape through the frangible portion 134.

The oxygen mask 100 may further include an oral access port 140 in the lower portion 104. The oral access port 140 may include a lumen 142 in communication with the chamber 101 and a bite block 144 extending around the lumen 142. The bite block 144 may include a tube extending inwardly from a center of the lower portion 104 into the chamber 101, such that the bite block 144 is positioned in-line with the mouth of the patient. The tube of the bite block 144 may be sufficiently rigid to prevent collapse when bitten down on to prevent damage of an instrument inserted through the lumen 142. In that sense, the tube of the bite block 144 may be made of a material more rigid than a material of the shell of the upper portion 102 and lower portion 104. The bite block 144 may have an upper portion 146 configured to engage teeth of an upper jaw of the patient and a lower portion 148 configured to engage teeth of a lower jaw of the patient. The upper and lower portions 146, 148 may be separated on each lateral side by a channel 150, the channel 150 being in communication with the lumen 142 and the chamber 101. Each of the upper and lower portions 146, 148 may have a slight curvature to facilitate insertion of the instrument with minimal interference. The bite block 144 may include a rigid flange 152 around the lumen 142 that is welded or adhered to the shell of the lower portion 104.

The bite block 144 may be adjustable to fit men, women, and/or children having faces of varied sizes and shapes. The adjustability may be provided by at least one fold or crease 180 each enclosing a well 182. The at least one fold or crease 180 may be compressible or flexible to allow the bite block 144 to vertically tilt or pivot at an angle α relative to a horizontal axis (as illustrated in FIG. 6) and/or to translate along the vertical and/or lateral axes of the oxygen mask 100. The at least one fold or crease 180 may be in the shell and allow the angle α be vertically tilted or pivoted up to about 5-8 degrees relative to the horizontal axis to fit the varied face sizes and shapes. Thus, the bite block 144 may extend at an acute angle α relative to the horizontal axis. The at least one fold or crease 180 may, additionally or alternatively, be compressed along the vertical and/or lateral axes to allow the bite block to translate along the vertical and/or lateral directions to further adjust the oxygen mask 100 to the varied facial sizes and shapes. The at least one fold or crease 180 and enclosed well 182 may have a substantially U- or V-shaped cross-section. In some embodiments, the at least one fold or crease 180 may be inelastic to maintain the adjustment (pivot angle and/or translation distance) without immediately reverting back to the original configuration, so the bite block 144 may be adjusted prior to being placed on the patient. However, in some embodiments, the at least one fold or crease 180 may be elastic to revert the bite block 144 back to the original configuration but still provide flexibility to accommodate the adjustment.

The at least one fold or crease 180 may extend circumferentially around a longitudinal axis of the bite block 144 to allow for the tilting and/or translation. Thus, the at least one fold or crease 180 may extend above and below the oral access port 140 and laterally overlap with the oral access port 140. The circumferential configuration allows the at last one fold or crease 180 be a single fold or crease 180 defining a single well 182 that allows the tilting and translation of the bite block 144 in the vertical and lateral directions. The rigid flange 152 of the bite block 144 may be disposed within a recess inside of the circumferential fold or crease 180.

Figure 4:
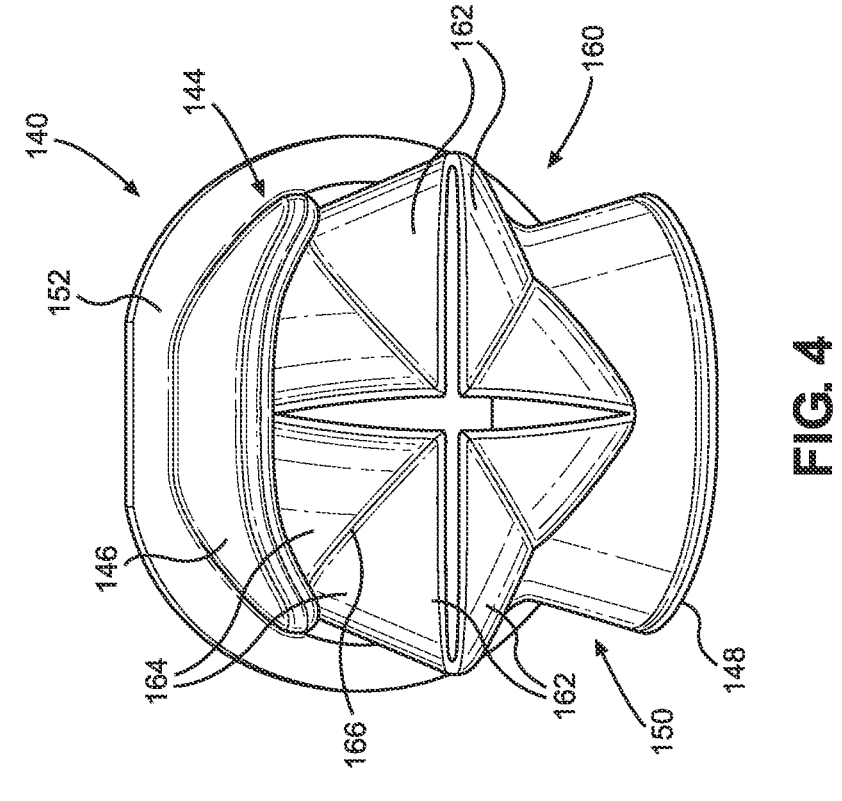
FIG. 4 illustrates an exemplary rear view of a bite block of the oxygen mask of FIGS. 1-3.
Figure 3:
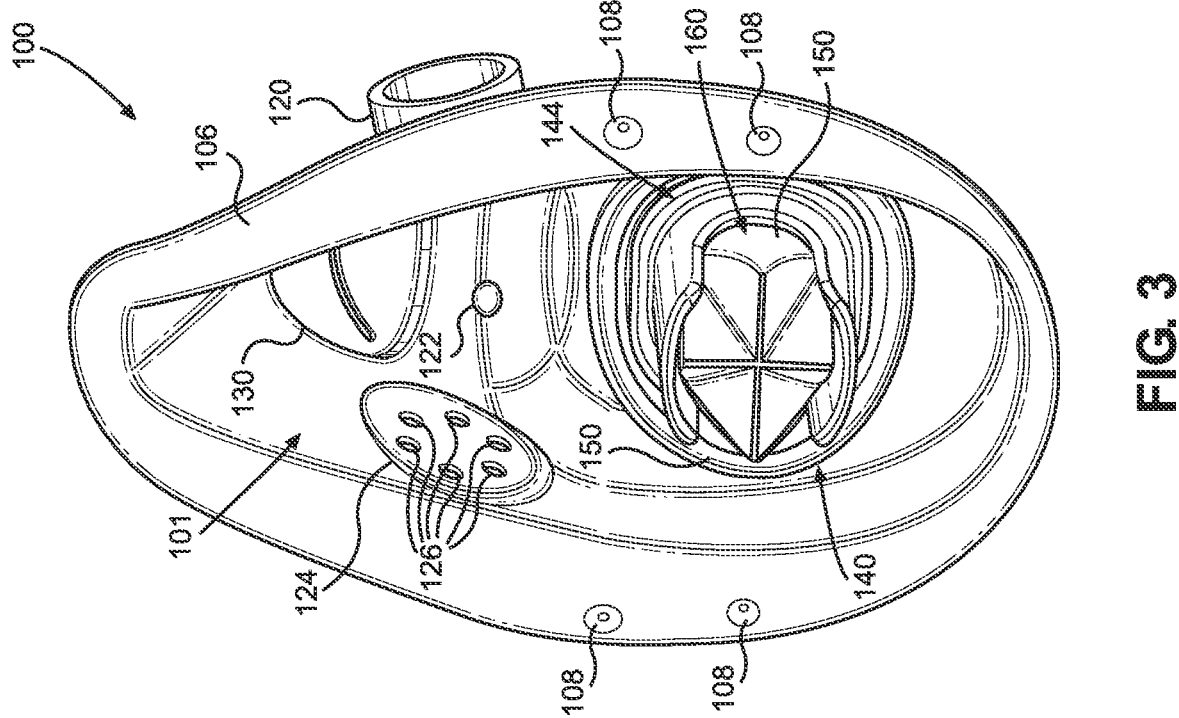
FIG. 3 illustrates an exemplary rear isometric view of the oxygen mask of FIGS. 1 and 2.

The bite block 144 may have a one-way valve 160 across the lumen 142 that defines an open configuration and a closed configuration. In the open configuration, the one-way valve 160 may allow passage of an instrument through the lumen 142 into the chamber 101. In the closed configuration, the one-way valve 160 may substantially seal the lumen 142 and the chamber 101 in an airtight manner. The one-way valve 160 may be a duckbill valve formed of a plurality of valve members 162 (e.g., four valve members 162 as illustrated) biased into the closed configuration in engagement with or closely approximate each other. The duckbill valve 160 may be integrated into the bite block 144 and provide a robust, self-sealing mechanism that does not require valve seating. Each of the valve members 162 may be formed of two substantially flat portions 164 converging at an apex 166 (as illustrated in FIG. 4). The valve 160 may be disposed between the face of the patient and shell of the lower portion 104, and inside of the lumen 142 of the bite block 144 to prevent interference from the teeth of the patient. Furthermore, when oxygen supply to the patient is insufficient or disrupted, the valve 160 may further serve as a safety valve which opens under negative pressure within the face mask to allow ambient room air to enter the mask 100 during the inspiratory cycle.

The oxygen mask 100 may include a plurality of holes 108 in the rim 106 for securing one or more straps 502, as illustrated in FIGS. 7 and 8. The straps 502 may be elastic and fit around the head of the patient to secure the oxygen mask 100 over the nose and mouth of the patient. For example, two straps 502 may each be separately threaded through a pair of holes 108, such that each of the straps 502 may be tightened to sealingly secure the oxygen mask 100 on the patient, as illustrated in FIGS. 7 and 8.

As further illustrated in the systems 500, 500' of FIGS. 7 and 8, the oxygen supply port 120 may be coupled to a supply adaptor 504 for supply of oxy gen. The oxygen supply port 120 may be integrated into the shell of the oxygen mask 100 in a peripheral sidewall on a first side of the upper portion 102. The oxygen supply port 120 may be an open tubular member having a diameter larger than the supply adaptor 504 and configured to receive the supply adaptor 504 in a tight fit. For example, as illustrated in the embodiment of FIG. 7, the supply adaptor 504 may be connected to an oxygen supply line 506 and configured for medium concentration oxygen flow. FIG. 8 illustrates an embodiment having a supply adaptor 504' connected to the oxygen supply line 506 and a reservoir bag 508 to be configured for high concentration oxygen flow or a non-rebreathing mask. The supply adaptor 504' may fit radially around a fitting of the reservoir bag 508. The oxygen supply line 506 in either of the systems 500, 500' may have a fitting 507 to be connected to an oxygen tank (not shown) for the supply of flow regulated oxygen to the chamber 101.

The sampling port 122 may be positioned on a front face of the upper portion 102 and in communication with the chamber 101. The sampling port 122 may be configured for sampling of the air in the chamber 101 to determine the level of carbon dioxide during use. The sampling port 122 may have a diameter ranging from about 2.5 mm to about 3.7 mm. In some embodiments, the sampling port 122 may be covered by a cap 510.

The exhalation port 124 may be integrated into the shell of the oxygen mask 100 in a peripheral sidewall on a second side of the upper portion 102, laterally opposite of the oxygen supply port 120. The exhalation port 124 may have a circular shape with a plurality of holes 126 around a circumference (e.g., six holes 126 as illustrated). The holes 126 may allow carbon dioxide rich exhaled air leave the oxygen mask 100. When configured as a non-rebreathing mask, the exhalation port 124 may be fitted with a flap valve (not shown) to block room/ambient air from entering into the oxygen mask 100. The flap valve may be circular to cover the holes 126, and deflect away from the holes 126 wider positive pressure from the chamber 101 to allow the carbon dioxide rich exhaled air to leave the oxygen mask 100. The flap valve may be supported and retained at its center by having a central aperture that receives a post 128 of the exhalation port 124. When configured for medium concentration or high concentration oxygen flow, the exhalation port 124 may be left open with no flap valve. Thus, the exhalation port 124 would allow ambient room air intake to combine with oxygen intake from the oxygen supply port 120 to provide all of the total patient inspiratory flow.

The system 500, 500' may further include a nose clip 520 securable to the upper portion 102. The nose clip 520 may have a substantially "U" shape. The nose clip 520 may be crimpable and/or spring-biased to compress the upper portion 102 around the nose of the patient. The nose clip 520 may have openings on its ends configured to receive posts 170 integrated into the upper portion 102 to secure the nose clip 520 to the oxygen mask 1M. Although the systems 500, 500' are illustrated with the oxygen mask 100, the systems 500, 500' may alternatively include oxygen mask 200, 300, as further discussed below.

Figures 9, 10:
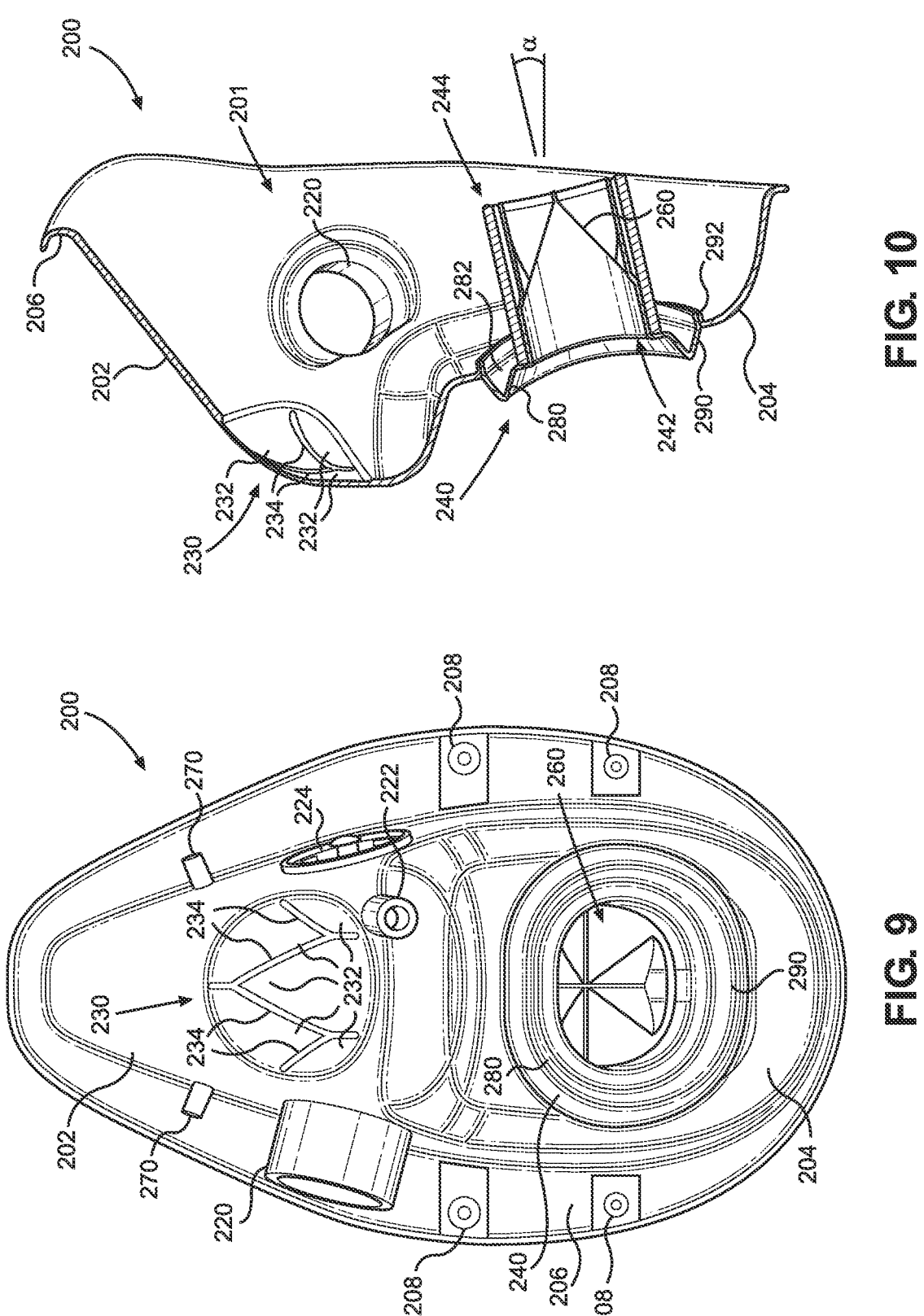
FIG. 9 illustrates an exemplary frontal view of a second embodiment of an oxygen mask according to the present invention.
FIG. 10 illustrates an exemplary side cross-sectional view of the oxygen mask of FIG. 9.

FIGS. 9 and 10 illustrate an oxygen face mask 200 according to a second exemplary embodiment of the present invention. The oxygen mask 200 is a variation of the oxygen mask 100 and thus embodies a number of the features of the oxygen mask 100, as discussed herein, and indicated with reference numbers having the same last two digits. Thus, the disclosure of the oxygen mask 100 is expressly incorporated herein with regard to the oxygen mask 200, unless expressly indicated otherwise.

For example, as further discussed above, the oxygen mask 200 may include an upper portion 202 and a lower portion 204 defining a chamber 201 that fits over the face of a patient to provide oxygen-rich air. The upper portion 202 may have a convexity to fit over a nose of the patient with sufficient space for comfort. The lower portion 204 may be configured to fit over a mouth of the patient. A rim 206 may extend at least partially (e.g. fully) around the upper portion 202 and the lower portion 204. In use, the rim 206 may engage the face of the patient to create an air-tight seal when the oxygen mask 200 generally envelops the nose and mouth of the patient in the chamber 201. The rim 206 may have a plurality of holes 208 for securing one or more straps 502 (as illustrated in FIGS. 7 and 8) to sealingly secure the oxygen mask 200 on the patient. The mask 200 may also have posts 270 integrated into the upper portion 202 to secure the nose clip 520 to the oxygen mask 200. The oxygen mask 200 may have one or more inlets and/or outlets in communication with the chamber 201 to deliver oxygen-rich air to the patient. For example, the oxygen mask 200 may include an oxygen supply port 220 providing an inlet to the chamber 201, a sampling port 222 providing an outlet of the chamber 201, and an exhalation port 224 providing an outlet of the chamber 201, as further discussed herein with reference to FIGS. 7 and 8.

The oxygen mask 200 may include a nasal access port 230 in the upper portion 202. The nasal access port 230 may be penetratable and/or puncturable. For example, as illustrated, the nasal access port 230 may include one or more flaps 232 connected by one or more frangible portions 234 along at least a portion of the edges of the one or more flaps 232. The one or more frangible portion 234 may be normally intact to ensure the one or more flaps 232 are held together and seal the nasal access port 230, preventing the release of gas therethrough. The one or more frangible portions 234 may be made of a different material (e.g., a softer or weaker material) and/or have reduced material strength provided by a reduced thickness, compared to the one or more flaps 232 and/or shell of the oxygen mask 200. In some embodiments, the one or more frangible portions 234 may be an adhesive or weld connecting the one or more flaps 232. The one or more frangible portions 234 may be selectively torn or broken to separate the one or more flaps 232 to provide one or more access openings to the nasal passage(s) for insertion of an instrument (e.g., a catheter, an endoscope, and/or a probe). The one or more flaps 232 may be biased in the naturally closed configuration. Thus, the one or more flaps 232 may be sufficiently flexible to conform around the inserted instrument to ensure that the chamber 201 is sealed and revert back into the closed configuration after the instrument is removed. As further illustrated, the one or more frangible portions 234 and/or edges of the one or more flaps 232 may form a plurality of lines. The plurality of lines may include at least two lines (e.g. three or more lines) connected to each other at an angle in a non-perpendicular orientation, extending at acute and/or obtuse angles relative to each other (e.g., in a non-"+" or "X" shape). The plurality of lines may be laterally spaced and connected by a plurality of nodes, one or more of the nodes may provide access to each nasal cavity. For example, the plurality of lines may include a first line and a second line that are connected at a first node (e.g., forming a first "V" shape) in-line and providing access to a right nasal cavity and a third line and a fourth line that are connected at a second node (e.g., forming a second "V" shape) in-line and providing access to a left nasal cavity. The second line and the third line may optionally be connected at a third node joining the first and second "V" shapes and forming a "W" shape or a zigzag shape. It is also contemplated that the nodes may be rounded to form "U" shapes and/or a sinusoidal shape. An additional line can extend vertically (upward or downward) from each of the nodes to facilitate opening of the nodes and insertion of an instrument. This configuration further enables the first node and the second node of the nasal access port 230 to be independently or separately penetrated and/or punctured to independently access either the right or left nasal cavity. The first node may be penetrated and/or punctured to access the right nasal cavity while the second node remains intact or approximated to prevent escape of oxygen. Alternatively, the second node may be penetrated and/or punctured to access the left nasal cavity while the first node remains intact or approximated to prevent escape of oxygen. Furthermore, a portion of each of the lines may be separately penetrated and/or punctured while another portion of the same line remains intact or approximated.

In some embodiments with the one or more frangible portions 234, the nasal access port 230 may have a continuous, flexible, modifiable membrane formed by the one or more flaps 232 when the one or more frangible portions 234 are intact, from which one or more customized instrument-access openings may be manually constructed when and if needed, by puncturing one or more lengths of the one or more frangible portions 234 to access either or both of the right and left nasal cavities of the patient.

In some embodiments, the one or more frangible portions 234 may be omitted, such that the edges of the one or more flaps 232 may be approximated to produce small gaps providing a sufficient seal to reduce gas leakage. The small gaps formed between the one or more flaps 232 and the inserted instrument resulting with a minor amount of gas leakage in and out of the oxygen mask 200; however, the gas leakage through the small gaps would be negligible compared to the oxygen made available to the patient through the oxygen supply port 220. The small gaps between the one or more flaps 232 may form lines having the same orientation as the one or more frangible portions 234. In some embodiments, the one or more flaps 232 may be omitted, and the membrane covering the nasal access port 230 may be a single, continuous frangible portion 234 (not illustrated) allowing for completely customizable access openings of any size and shape through the frangible portion 234. Alternatively, the frangible portions 234 may be formed just at one or more of the nodes (e.g., all the nodes) to connect the one or more flaps 232 and retain the shape of the nasal access port 230 during shipping and storage.

The oxygen mask 200 may further include an oral access port 240 in the lower portion 204. The oral access port 240 may include a lumen 242 in communication with the chamber 201 and a bite block 244 extending around the lumen 242. The bite block 244 may be adjustable to fit men, women, and/or children having faces of varied sizes and shapes. The adjustability may be provided by at least one fold or crease 280 each enclosing a well 282. The at least one fold or crease 280 may be compressible to allow the bite block 244 to vertically tilt or pivot at an angle α relative to a horizontal axis (as illustrated in FIG. 10) and/or to translate along the vertical and/or lateral axes of the oxygen mask 200. Thus, the bite block 244 may be adjusted at the acute angle α relative to the horizontal axis. The at least one fold or crease 280 may, additionally or alternatively, be compressed along the vertical and/or lateral axes to allow the bite block to translate along the vertical and/or lateral directions to further adjust the oxygen mask 200 to the varied facial sizes and shapes. The at least one fold or crease 280 and enclosed well 282 may have a substantially U- or V-shaped cross-section without any overlying rib structures. The bite block 244 may have a one-way valve 260 across the lumen 242 that defines an open configuration and a closed configuration, as discussed herein.

The at least one fold or crease 280 may extend circumferentially around a longitudinal axis of the bite block 244 to allow for the tilting (or pivoting) and/or translation. Thus, the at least one fold or crease 280 may extend above and below the oral access port 240 and laterally overlap with the oral access port 240. The circumferential configuration allows the at last one fold or crease 280 be a single fold or crease 280 defining a single well 282 that allows the tilting and translation of the bite block 244 in the vertical and lateral directions. The at least one fold or crease 280 may be formed by a membrane 290 connecting a translatable end of the bite block 244 to the shell of the lower portion 204. The membrane 290 may be sufficiently flexible to allow for increased adjustment of the bite block 244 relative to the shell of the lower portion 204. For example, the membrane 290 may be formed of a material that is softer than that of the shell of the lower portion 204 and/or have a thickness less than that of the shell of the lower portion 204. The membrane may allow the at least one fold or crease 280 at the angle α up to about 25 degrees relative to the horizontal axis to fit the varied face sizes and shapes. The membrane 290 may be inelastic and sufficiently rigid to retain the bite block 244 in place after adjustment without immediately reverting back to the original configuration, so the bite block 244 may be adjusted prior to being placed on the patient. However, in some embodiments, the oxygen mask 200 may elastically revert the bite block 244 back to the original configuration but still provide flexibility to accommodate the adjustment. The membrane 290 may have a radially outer surface welded to the shell of the lower portion at an edge joint 292 and a radially inner surface welded to the bite block 244, for example, each with a radiofrequency (RF) weld.

Figure 12:
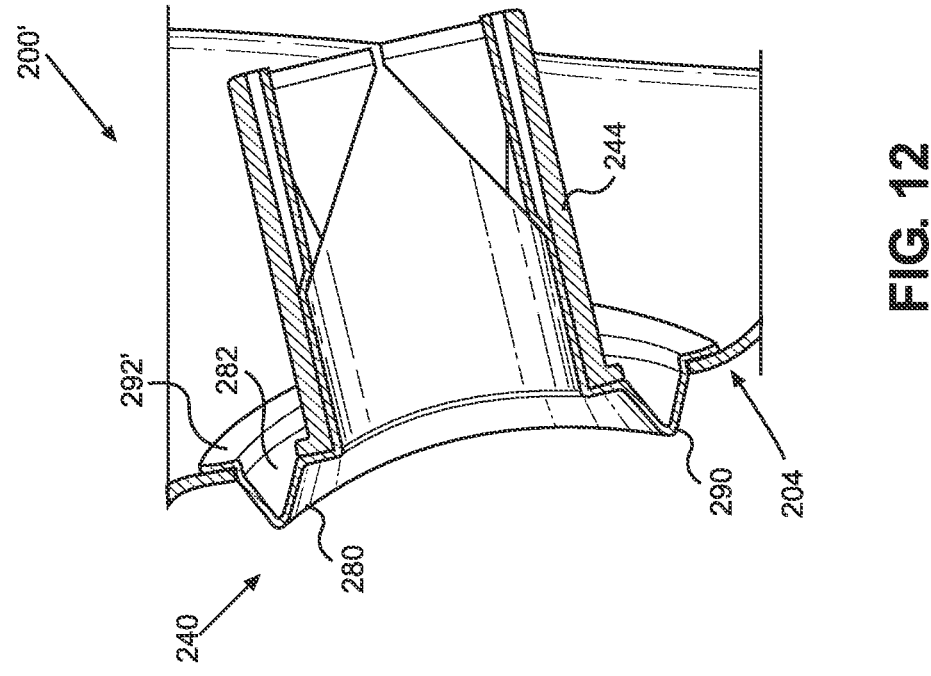
FIG. 12 illustrates an exemplary side cross-sectional partial view of the oxygen mask of FIG. 11.
Figure 11:
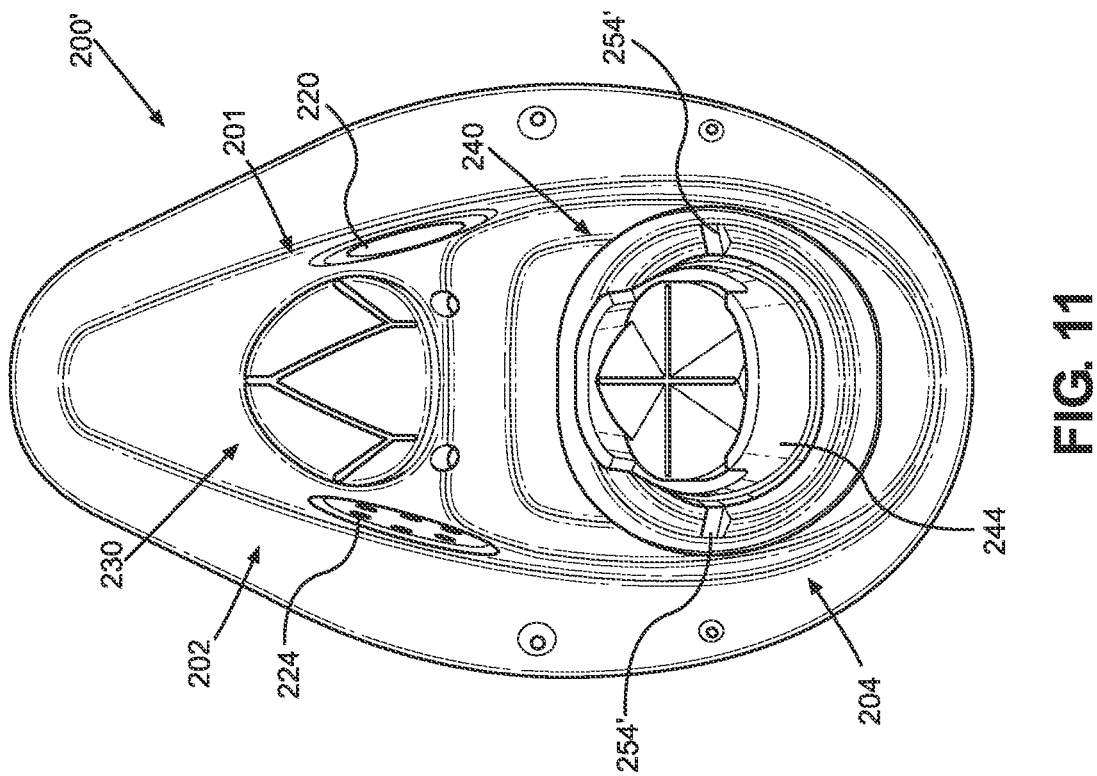
FIG. 11 illustrates an exemplary rear view of a third embodiment of the oxygen mask according to the present invention.

FIGS. 11 and 12 illustrate an oxygen mask 200' according to a third exemplary embodiment of the present invention. The oxygen mask 200' is a variation of the oxygen mask 200 and thus embodies a number of the features of the oxygen mask 100, 200, as discussed herein, and indicated with the reference numbers of the oxygen mask 200. Thus, the disclosure of the oxygen mask 100, 200 is expressly incorporated herein with regard to the oxygen mask 200', unless expressly indicated otherwise. For example, as further discussed above, the oxygen mask 200' may include an upper portion 202' and a lower portion 204' defining a chamber 201' that fits over the face of a patient to provide oxygen-rich air, as discussed herein.

As further illustrated in FIG. 11, the oxygen mask 200' may include one or more ribs 254' extending radially across the well 282 of the at least one fold or crease 280 to prevent vertical and/or lateral translation of the bite block 244. As illustrated in FIG. 11, the one or more ribs 254' may include a pair of ribs 254' extending laterally on opposite lateral sides of the bite block 244. The lateral positioning of the ribs 254' (and absence of ribs 254' in the vertical direction) may substantially fix the distal end of the bite block 244 laterally relative to the lower portion 204 while allowing the bite block 244 to tilt or pivot up and down in the vertical direction about the fixed attachment. The one or more ribs 254' may increase the stability of the bite block 244 ensuring that the bite block 244 maintains position in the oral cavity after the oxygen mask 200' is strapped to the patient. As further illustrated in FIG. 12, the periphery of the membrane 290 may laterally overlap the shell at the lower portion 204 to be joined at a lap joint 292', for example, with an RF weld.

Figures 13, 14:
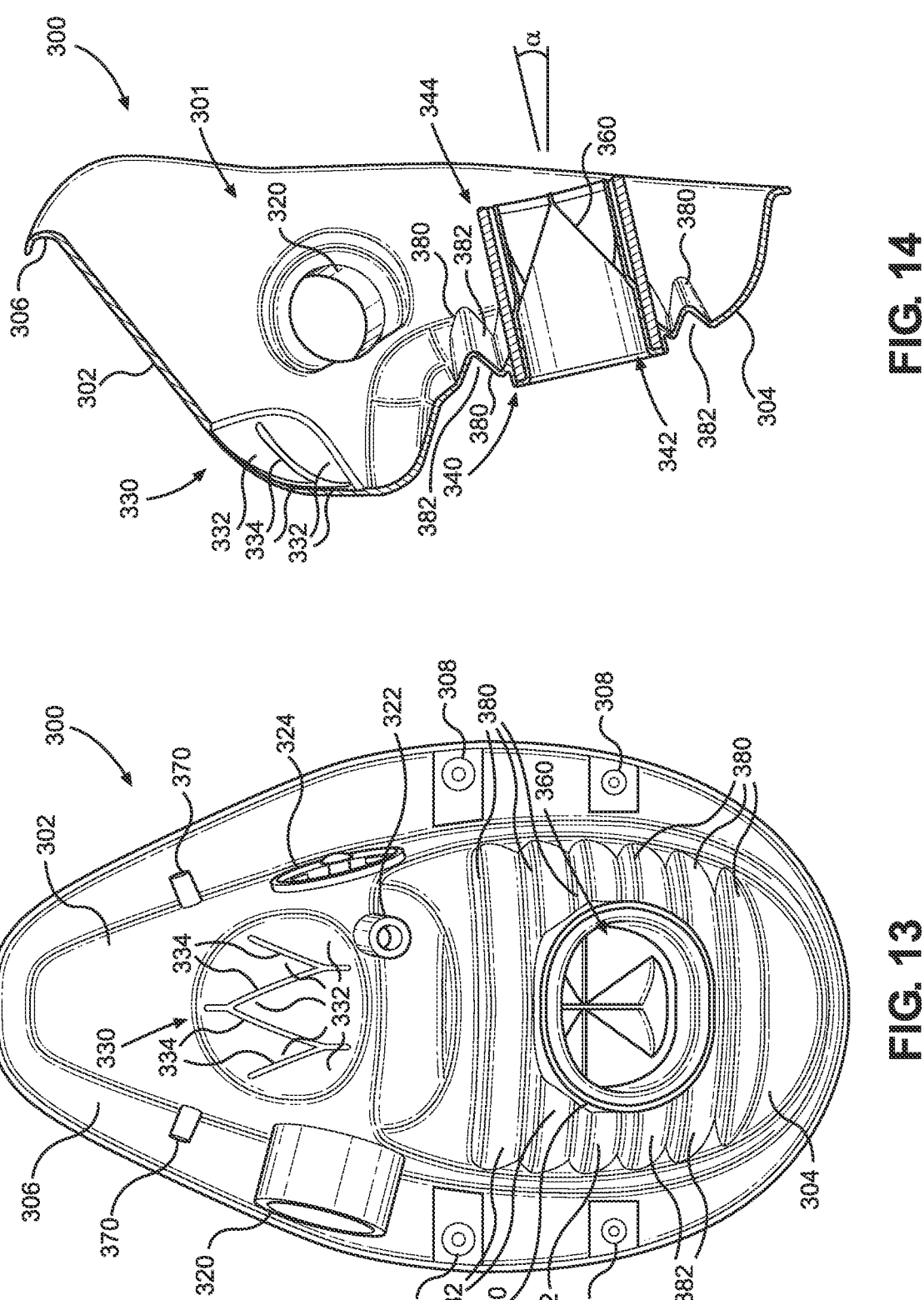
FIG. 13 illustrates an exemplary frontal view of a fourth embodiment of the oxygen mask according to the present invention.
FIG. 14 illustrates an exemplary side cross-sectional view of the oxygen mask of FIG. 13.

FIGS. 13 and 14 illustrate an oxygen mask 300 according to a fourth exemplary embodiment of the present invention. The oxygen mask 300 may embody a number of the features of the oxygen mask 100, 200, 200', as discussed herein, and indicated with reference numbers having the same last two digits. Thus, the disclosure of the oxygen mask 100, 200, 200' is expressly incorporated herein with regard to the oxygen mask 300, unless expressly indicated otherwise.

For example, as further discussed above, the oxygen mask 30) may include an upper portion 302 and a lower portion 304 defining a chamber 301 that fits over the face of a patient to provide oxygen-rich air. The upper portion 302 may have a convexity to fit over a nose of the patient with sufficient space for comfort. The lower portion 304 may be configured to fit over a mouth of the patient. A rim 306 may extend at least partially (e.g. fully) around the upper portion 302 and the lower portion 304. In use, the rim 306 may engage the face of the patient to create an air-tight seal when the oxygen mask 300 generally envelops the nose and mouth of the patient in the chamber 301. The rim 306 may have a plurality of holes 308 for securing one or more straps 502 (as illustrated in FIGS. 7 and 8) to sealingly secure the oxygen mask 300 on the patient. The mask 300 may also have posts 370 integrated into the upper portion 302 to secure the nose clip 520 to the oxygen mask 300. The oxygen mask 300 may have one or more inlets and/or outlets in communication with the chamber 301 to deliver oxygen-rich air to the patient. For example, the oxygen mask 300 may include an oxygen supply port 320 providing an inlet to the chamber 301, a sampling port 322 providing an outlet of the chamber 301, and an exhalation port 324 providing an outlet of the chamber 301, as further discussed below with reference to FIGS. 7 and 8.

The oxygen mask 300 may include a nasal access port 330 in the upper portion 302. The nasal access port 330 may be penetratable and/or puncturable. For example, as illustrated, the nasal access port 330 may include one or more flaps 332 connected by one or more frangible portions 334 along at least a portion of the edges of the one or more flaps 332. The one or more frangible portion 334 may be normally intact to ensure the one or more flaps 332 are held together and seal the nasal access port 330, preventing the release of gas therethrough. The one or more frangible portions 334 may be made of a different material (e.g., a softer or weaker material) and/or have reduced material strength provided by a reduced thickness, compared to the one or more flaps 332 and/or shell of the oxygen mask 300. In some embodiments, the one or more frangible portions 334 may be an adhesive or weld connecting the one or more flaps 332. The one or more frangible portions 334 may be selectively torn or broken to separate the one or more flaps 332 to provide one or more access openings to the nasal passage(s) for insertion of an instrument (e.g., a catheter, an endoscope, and/or a probe). The one or more flaps 332 may be biased in the naturally closed configuration. Thus, the one or more flaps 332 may be sufficiently flexible to conform around the inserted instrument to ensure that the chamber 301 is sealed and revert back into the closed configuration after the instrument is removed. As further illustrated, the one or more frangible portions 334 and/or edges of the one or more flaps 332 may form a plurality of lines. The plurality of lines may include at least two lines (e.g., three or more lines)

connected to each other at an angle in a non-perpendicular orientation, extending at acute and/or obtuse angles relative to each other (e.g., in a non-"+" or "X" shape). The plurality of lines may be laterally spaced and connected by a plurality of nodes, one or more of the nodes may provide access to each nasal cavity. For example, the plurality of lines may include a first line and a second line that are connected at a first node (e.g., forming a first "V" shape) in-line and providing access to a right nasal cavity and a third line and a fourth line that are connected at a second node (e.g., forming a second "V" shape) in-line and providing access to a left nasal cavity. The second line and the third line may optionally be connected at a third node joining the first and second "V" shapes and forming a "W" shape or a zigzag shape. It is also contemplated that the nodes may be rounded to form "U" shapes and/or a sinusoidal shape. An additional line can extend vertically (upward or downward) from each of the nodes to facilitate opening of the nodes and insertion of an instrument. This configuration further enables the first node and the second node of the nasal access port 230 to be independently or separately penetrated and/or punctured to independently access either the right or left nasal cavity. The first node may be penetrated and/or punctured to access the right nasal cavity while the second node remains intact or approximated to prevent escape of oxygen. Alternatively, the second node may be penetrated and/or punctured to access the left nasal cavity while the first node remains intact or approximated to prevent escape of oxygen. Furthermore, a portion of each of the lines may be separately penetrated and/or punctured while another portion of the same line remains intact or approximated.

In some embodiments with the one or more frangible portions 334, the nasal access port 330 may have a continuous, flexible, modifiable membrane formed by the one or more flaps 332 when the one or more frangible portions 334 are intact, from which one or more customized instrument-access openings may be manually constructed when and if needed, by puncturing one or more lengths of the one or more frangible portions 334 to access either or both of the right and left nasal cavities of the patient.

In some embodiments, the one or more frangible portions 334 may be omitted, such that the edges of the one or more flaps 332 may be approximated to produce small gaps providing a sufficient seal to reduce gas leakage. The small gaps formed between the one or more flaps 332 and the inserted instrument resulting with a minor amount of gas leakage in and out of the oxygen mask 300; however, the gas leakage through the small gaps would be negligible compared to the oxygen made available to the patient through the oxygen supply port 320. The small gaps between the one or more flaps 332 may form lines having the same orientation as the one or more frangible portions 334. Alternatively, the frangible portions 334 may be formed just at one or more of the nodes (e.g., all the nodes) to connect the one or more flaps 334 and retain the shape of the nasal access port 330 during shipping and storage.

In some embodiments, the one or more flaps 332 may be omitted, and the membrane covering the nasal access port 330 may be a single, continuous frangible portion 334 (not illustrated) allowing for completely customizable access openings of any size and shape through the frangible portion 334.

The oxygen mask 300 may include a bite block 344 that is adjustable to fit men, women, and/or children having faces of varied sizes and shapes. The adjustability may be provided by at least one fold or crease 380 each enclosing a well 382. The at least one fold or crease 380 may be compressible to allow the bite block 344 to vertically tilt or pivot at an angle α relative to a horizontal axis (as illustrated in FIG. 14) and/or to translate along the vertical and/or lateral axes of the oxygen mask 300. The at least one fold or crease 380 may allow the angle α be vertically tilted in the up to about 11-15 degrees relative to the horizontal axis to fit the varied face sizes and shapes. Thus, the bite block 344 may extend at the acute angle α relative to the horizontal axis. The at least one fold or crease 380 may, additionally or alternatively, be compressed along the vertical and/or lateral axes to allow the bite block to translate along the vertical and/or lateral directions to further adjust the oxygen mask 300 to the varied facial sizes and shapes. The at least one fold or crease 380 and enclosed well 382 may have a substantially U- or V-shaped cross-section. In some embodiments, the at least one fold or crease 380 be inelastic to maintain the adjustment (pivot angle and/or translation distance) without immediately reverting back to the original configuration, so the bite block 344 may be adjusted prior to being placed on the patient. However, in some embodiments, the mask 300 may elastically revert the bite block 344 back to the original configuration but still provide flexibility to accommodate the adjustment.

The at least one fold or crease 380 may include a plurality of folds or creases 380 forming a bellowed and/or corrugated structure extending laterally from a first lateral portion to a second lateral portion. The plurality of folds or creases 380 may be stacked from below the oral access port 340 to above the oral access port 340, and the plurality of folds or creases 380 may extend inward and outward of the chamber 301 in an accordion style. Thus, the plurality of folds or creases 380 may include complete folds 380 above and below the oral access port 360 extending from the first lateral portion to the second lateral portion and folds or creases 380 that are laterally interrupted by the oral access port 340. Thus, the at least one fold or crease 380 may extend above and below the oral access port 340 and laterally overlap with the oral access port 340. The bellowed and/or corrugated folds or creases allow the bite block 344 to vertically tilt about the horizontal axis and adjust along the vertical axis to suit variations of anatomy. The bite block 344 may have a one-way valve 360 across the lumen 242 that defines an open configuration and a closed configuration, as discussed herein.

The shell of the oxygen mask 100, 200, 200', 300 of the present disclosure may be molded into a one-piece from transparent, flexible plastic material such as a polyvinyl chlorine (PVC) or thermoplastic polyurethane (TPU), having a wall thickness of about 1.25 mm. The membrane 290, 290' may be made of a softer plastic material than the shell, such as a PVC or TPU produced with a lower shore durometer. The bite block 144, 244, 244', 344 may be made of a stiffer, more rigid plastic material than the shell, such as polypropylene (PP) or acrylonitrile butadiene styrene (ABS), and attached through insert molding, adhesive, and/or welding.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A mask comprising:
a convex shell having an upper portion and a lower portion and defining a chamber;
a rim at least partially around the chamber;
a nasal access port in the upper portion that is penetratable and/or puncturable to provide access to the chamber;
an oral access port in the lower portion, the oral access port having a front opening, a rear opening and a lumen therebetween, and including a bite block defining the lumen, and further comprising a duckbill valve disposed in the lumen, and
at least one fold or crease extending circumferentially around a longitudinal axis of the bite block and configured to allow the bite block to tilt relative to a horizontal axis and to translate along a vertical axis
wherein the fold or crease is configured to maintain the tilt relative to the horizontal axis and the translation along the vertical axis upon adjustment.

2. The mask of claim 1, further comprising an inlet into the chamber, and an outlet from the chamber.

3. The mask of claim 2, wherein the outlet comprises a plurality of holes disposed around a post.

4. The mask of claim 1, further comprising a sampling port in communication with the chamber.

5. The mask of claim 1, further comprising at least one post on the upper portion configured to secure a nose clip.

6. The mask of claim 1, wherein the nasal access port includes one or more flaps having edges that form a plurality of lines.

7. The mask of claim 6, wherein the plurality of lines includes a first line and a second line that are connected at a first node and a third line and a fourth line that are connected at a second node.

8. The mask of claim 6, wherein the plurality of lines includes at least two lines that are connected to each other at an angle in a non-perpendicular orientation.

9. The mask of claim 6, wherein the plurality of lines includes a first line and a second line that are connected to form a first "V" shape.

10. The mask of claim 9, wherein the plurality of lines includes a third line and a fourth line that are connected to form a second "V" shape.

11. The mask of claim 10, wherein the second line and the third line are connected to form a "W" shape.

12. The mask of claim 6, wherein the one or more flaps are connected by one or more frangible portions along at least a portion of the edges.

13. The mask of claim 1, wherein the bite block extends at an acute angle relative to a horizontal axis of the mask.

14. The mask of claim 1, wherein the at least one fold or crease extends above and/or below the oral access port.

15. The mask of claim 1, wherein the at least one fold or crease laterally overlaps the bite block.

16. The mask of claim 1, wherein the at least one fold or crease includes a plurality of folds or creases.

17. The mask of claim 16, wherein the plurality of folds or creases extend laterally between a first side portion and a second side portion.

18. A mask comprising:
a convex shell having an upper portion and a lower portion and defining a chamber;
a rim at least partially around the chamber;
an inlet into the chamber;
an outlet from the chamber;
a sampling port in communication with the chamber;

a nasal access port in the upper portion that is penetratable and/or puncturable to provide access to the chamber; and an oral access port in the lower portion, the oral access port having a front opening and a rear opening and a lumen therebetween, and including a bite block defining the lumen and a duckbill valve in the lumen, and at least one fold or crease extending circumferentially around a longitudinal axis of the bite block and configured to allow the bite block to tilt relative to a horizontal axis and to translate along a vertical axis wherein the fold or crease is configured to maintain the tilt relative to the horizontal axis and the translation along the vertical axis upon adjustment.

19. A mask comprising:

a convex shell having an upper portion and a lower portion and defining a chamber;

a rim at least partially around the chamber;

an oral access port in the lower portion, the oral access port having a front opening and a rear opening and a lumen therebetween, and including a bite block defining the lumen and a duckbill valve in the lumen; and at least one fold or crease extending circumferentially around a longitudinal axis of the bite block and configured to allow the bite block to tilt relative to a horizontal axis and to translate along a vertical axis wherein the fold or crease is configured to maintain the tilt relative to the horizontal axis and the translation along the vertical axis upon adjustment.

20. The mask of claim 19, wherein the at least one fold or crease extends above and/or below the oral access port.

21. The mask of claim 19, wherein the at least one fold or crease laterally overlaps the bite block.

22. The mask of claim 19, wherein the at least one fold or crease further comprises a plurality of folds or creases.

23. The mask of claim 22, wherein the plurality of folds or creases extend laterally between a first side portion and a second side portion.

* * * * *